United States Patent [19]

Itakura

[11] Patent Number: 5,365,076
[45] Date of Patent: Nov. 15, 1994

[54] RADIATION IMAGE RECORDING APPARATUS

[75] Inventor: Toru Itakura, Kanagawa, Japan

[73] Assignee: Fuji Photo Film Co., Ltd., Kanagawa, Japan

[21] Appl. No.: 138,054

[22] Filed: Oct. 19, 1993

[30] Foreign Application Priority Data

Oct. 19, 1992 [JP] Japan ............................. 4-280121
Dec. 25, 1992 [JP] Japan ............................. 4-347091

[51] Int. Cl.⁵ .............................................. G01N 23/04
[52] U.S. Cl. ...................................... 250/582; 250/583
[58] Field of Search .................... 250/582, 583; 378/5, 378/157

[56] References Cited

U.S. PATENT DOCUMENTS

| | | | |
|---|---|---|---|
| 4,258,264 | 3/1981 | Kotera et al. | 250/484 |
| 4,276,473 | 6/1981 | Kato et al. | 250/327.1 |
| 4,315,318 | 2/1982 | Kato et al. | 364/515 |
| 4,356,398 | 10/1982 | Komaki et al. | 250/327.2 |
| 4,387,428 | 6/1983 | Ishida et al. | 364/414 |
| 4,851,679 | 7/1989 | Tamura et al. | 250/327.2 |
| 4,855,598 | 8/1989 | Ohgoda et al. | 250/327.2 |
| 4,859,849 | 8/1989 | Shimura et al. | 290/582 |

FOREIGN PATENT DOCUMENTS

| | | | |
|---|---|---|---|
| 56-11395 | 2/1981 | Japan | G21K 4/00 |
| 59-102227 | 6/1984 | Japan . | |
| 3238441 | 10/1991 | Japan | G03B 42/02 |

*Primary Examiner*—Paul M. Dzierzynski
*Assistant Examiner*—Richard Hanig
*Attorney, Agent, or Firm*—Sughrue, Mion, Zinn, Macpeak & Seas

[57] ABSTRACT

A radiation image recording apparatus comprises a sheet housing section, which supports and houses at least a single stimulable phosphor sheet therein and which is exposed to radiation carrying image information of an object, a radiation image of the object being thereby stored on the stimulable phosphor sheet, which is housed in the sheet housing section. The sheet housing section is divided into at least three sheet housing compartments by a radiation energy distribution separating filter, which has good absorption characteristics with respect to low energy components of radiation and which is located in a direction approximately normal to the direction of travel of the radiation carrying image information of the object, and at least a single radiation transmitting member, which has good radiation transmitting characteristics and which is located parallel to the radiation energy distribution separating filter and at a position closer to the object than the radiation energy distribution separating filter is. Radiation images for energy subtraction processing or superposition processing are thereby obtained easily.

5 Claims, 11 Drawing Sheets

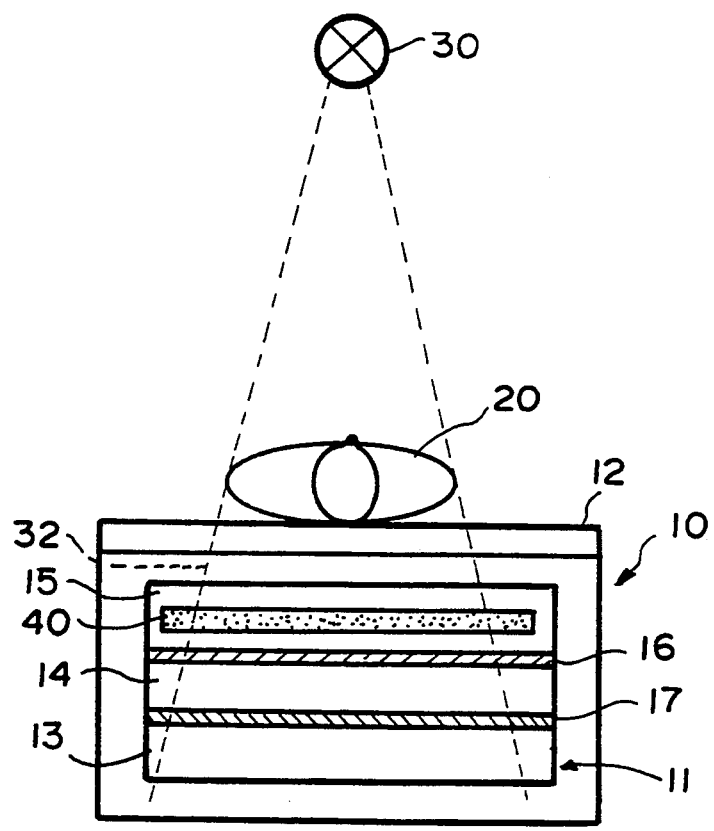

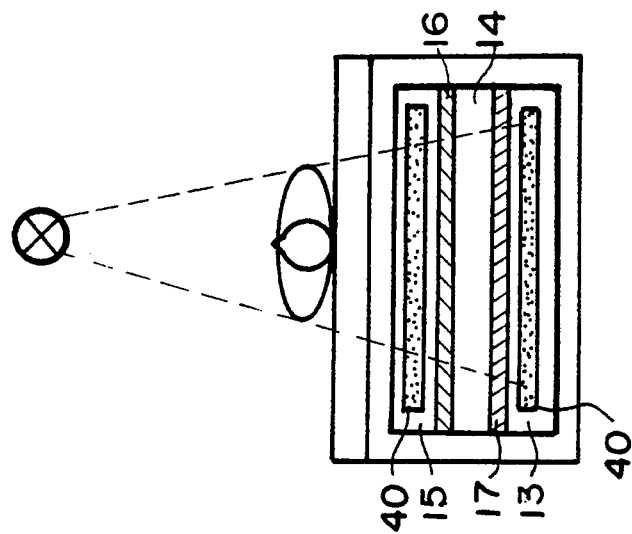
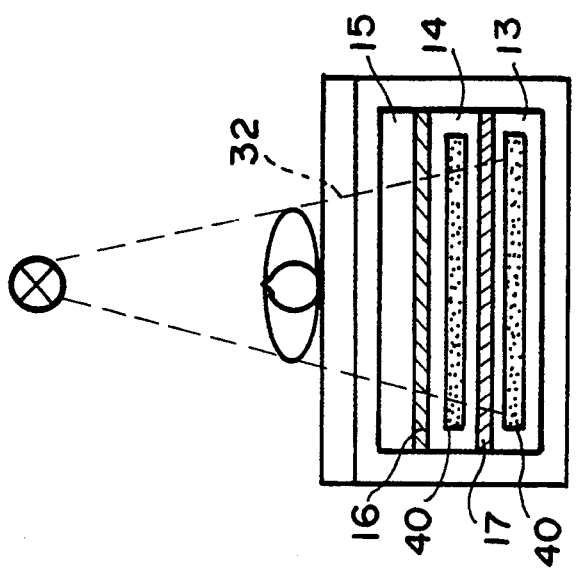
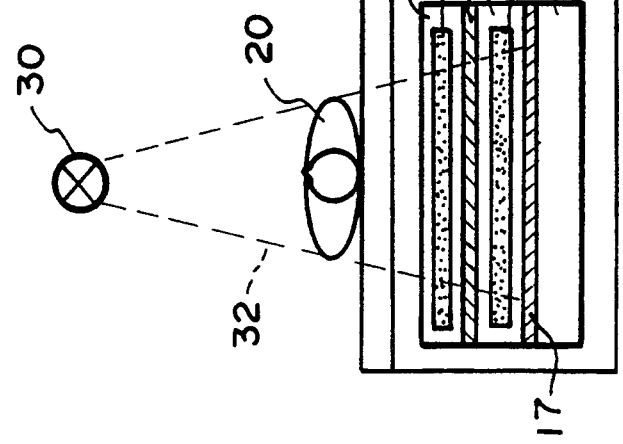

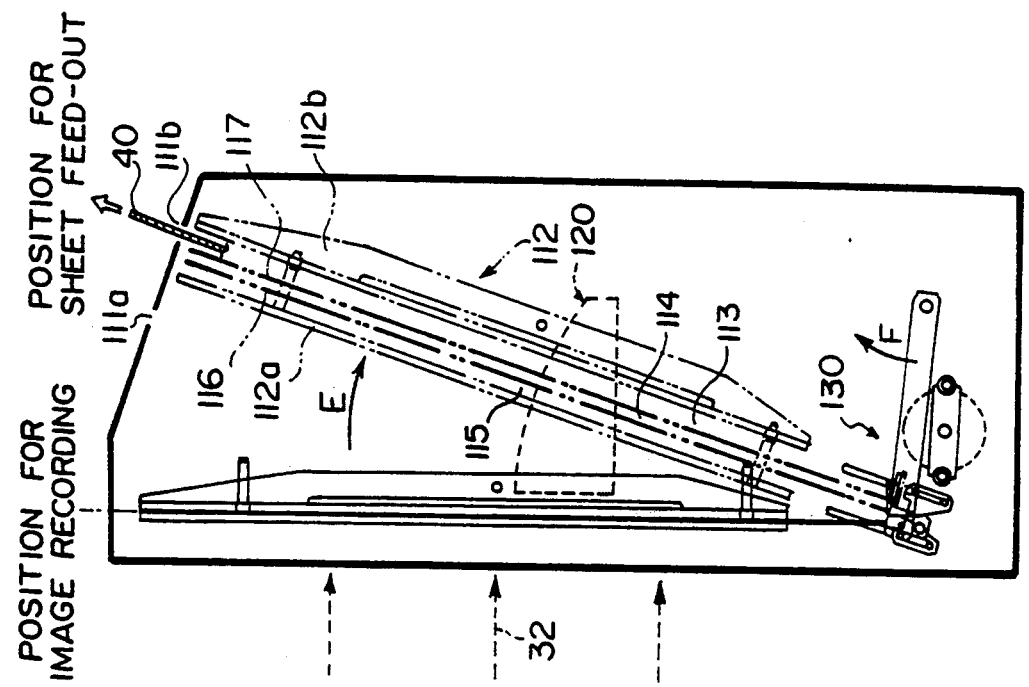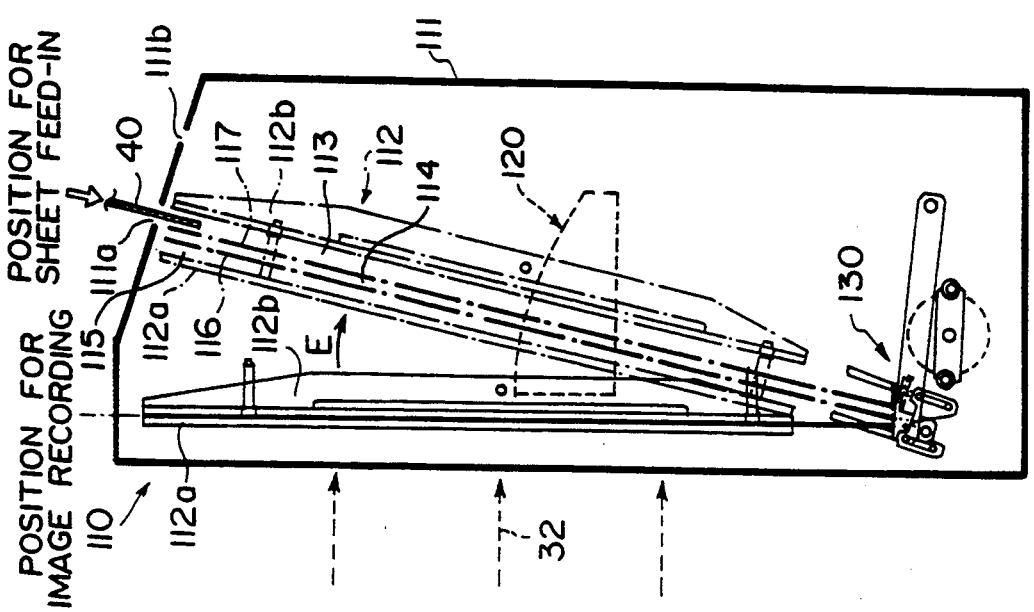

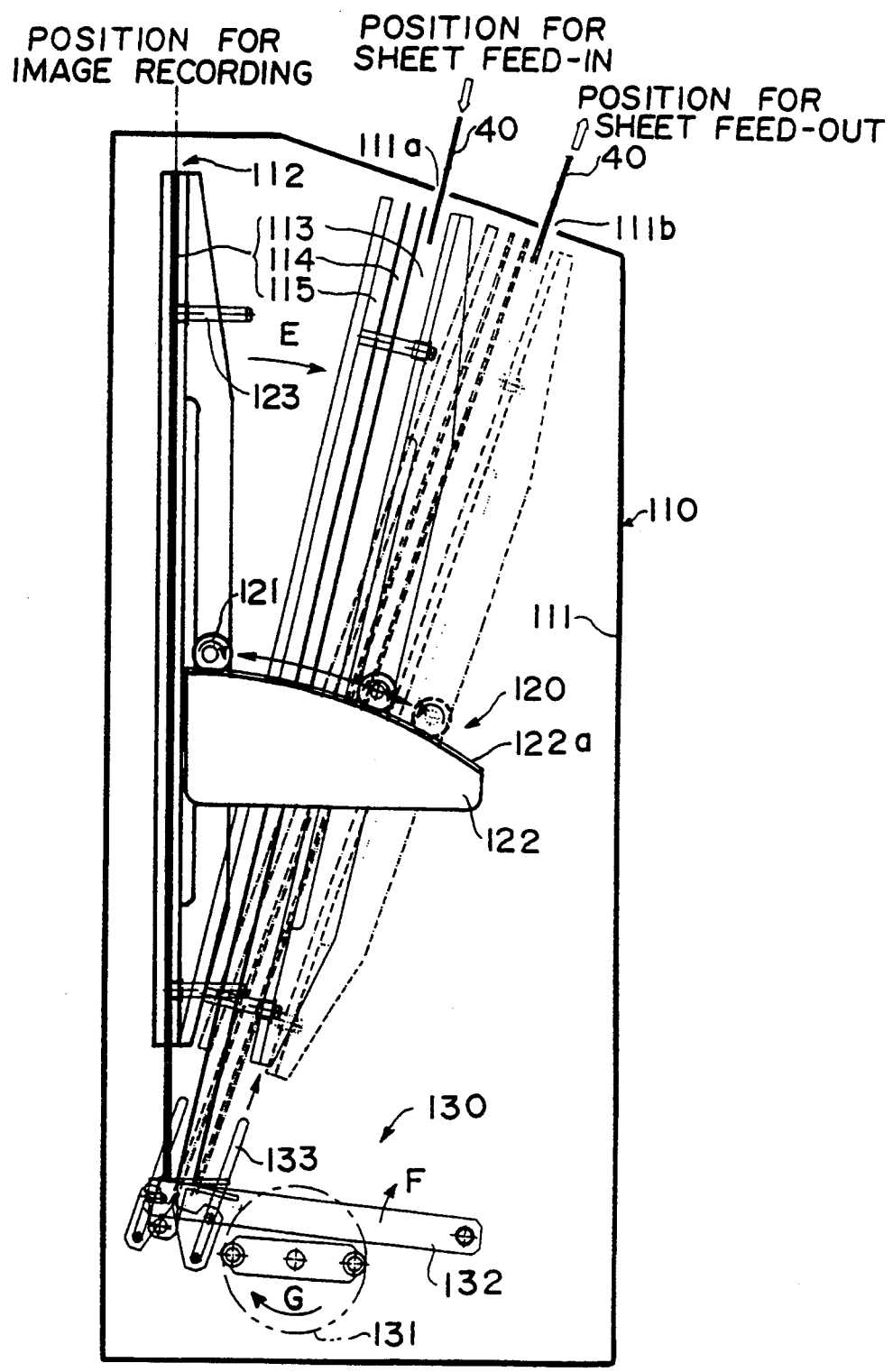

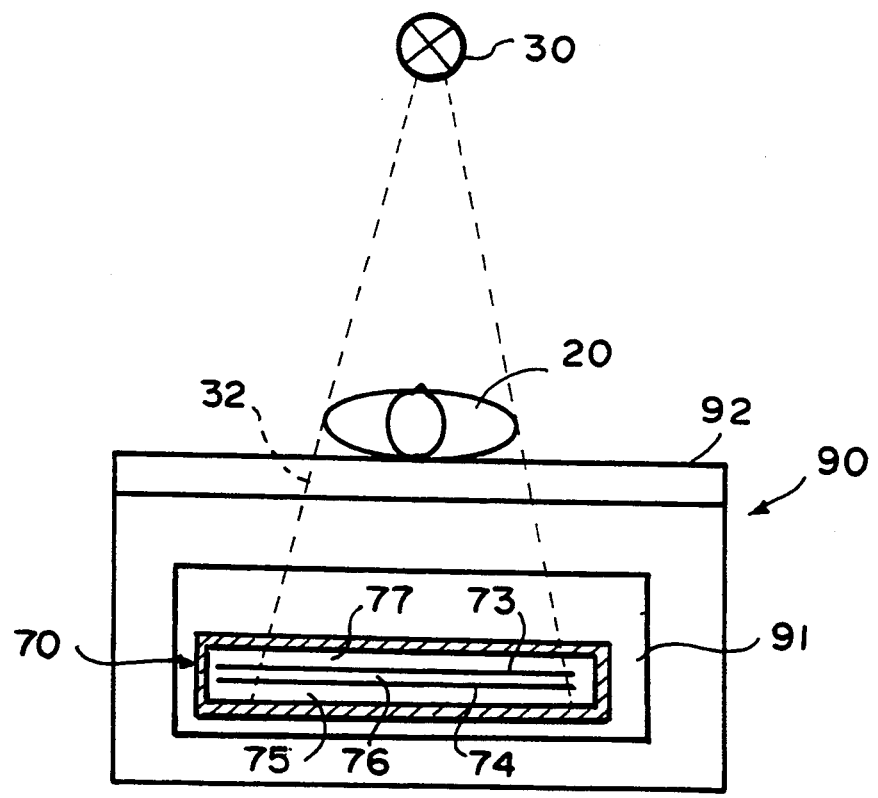

RADIATION IMAGE RECORDING APPARATUS

BACKGROUND OF THE INVENTION

1. Field of the Invention

This invention relates to a radiation image recording apparatus for storing a radiation image of an object on a stimulable phosphor sheet. This invention also relates to a radiation image recording and read-out apparatus for storing a radiation image of an object on a stimulable phosphor sheet and thereafter photoelectrically reading out the radiation image from the stimulable phosphor sheet. This invention further relates to a cassette for housing at least a single stimulable phosphor sheet during an operation for storing a radiation image on the stimulable phosphor sheet. This invention particularly relates to a radiation image recording apparatus, a radiation image recording and read-out apparatus, and a cassette, wherein radiation images to be subjected to energy subtraction processing and radiation images to be subjected to superposition processing are stored on stimulable phosphor sheets easily and selectively.

2. Description of the Prior Art

When certain kinds of phosphors are exposed to radiation such as X-rays, $\alpha$-rays, $\beta$-rays, $\gamma$-rays, cathode rays or ultraviolet rays, they store part of the energy of the radiation. Then, when the phosphor which has been exposed to the radiation is exposed to stimulating rays, such as visible light, light is emitted by the phosphor in proportion to the amount of energy stored thereon during its exposure to the radiation. A phosphor exhibiting such properties is referred to as a stimulable phosphor.

A radiation image recording apparatus, which utilizes a sheet provided with a layer of the stimulable phosphor (hereinafter referred to as a stimulable phosphor sheet), has been disclosed in, for example, Japanese Unexamined Patent Publication No. 59(1984)-102227. With the disclosed radiation image recording apparatus, a stimulable phosphor sheet is housed at a position for image recording and exposed to radiation carrying image information, and a radiation image of the object is thereby stored on the stimulable phosphor sheet.

Also, cassettes for housing a stimulable phosphor sheet therein have heretofore been known. The cassette is constituted of a box member provided with an opening, through which a stimulable phosphor sheet is to be fed into and out of the box member, and a cover member, which opens and closes the opening. The cassette houses the stimulable phosphor sheet in the box member and prevents the stimulable phosphor sheet, on which no radiation image has been stored, from being exposed to light before the stimulable phosphor sheet is used during an operation for recording a radiation image. Also, the cassette prevents the stimulable phosphor sheet, on which a radiation image has been stored, from being exposed to light before the stimulable phosphor sheet is subjected to an operation for reading out the radiation image.

Further, as disclosed in, for example, U.S. Pat. Nos. 4,258,264, 4,276,473, 4,315,318, 4,387,428, and Japanese Unexamined Patent Publication No. 56(1981)-11395, the applicant proposed various radiation image recording and reproducing systems, which utilize stimulable phosphor sheets. Specifically, a stimulable phosphor sheet, on which a radiation image has been stored, is exposed to stimulating rays, such as a laser beam, which cause it to emit light in proportion to the amount of energy stored thereon during its exposure to radiation. The light emitted by the stimulable phosphor sheet, upon stimulation thereof, is photoelectrically detected and converted into an electric image signal. A laser beam is then modulated with the image signal, and a photosensitive recording material or a thermosensitive recording material is two-dimensionally scanned with the modulated laser beam. In this manner, the radiation image is reproduced as a visible image on the recording material.

With the proposed radiation image recording and reproducing systems, radiation images can be recorded even when the energy intensity of the radiation, to which the stimulable phosphor sheet is exposed, varies over a wide range. Also, visible radiation images can be obtained which have good image quality and can serve as an effective tool in, particularly, the efficient and accurate diagnosis of an illness.

Also, the applicant proposed radiation image recording and read-out apparatuses, which efficiently process stimulable phosphor sheets, in, for example, U.S. Pat. No. 4,851,679 and Japanese Unexamined Patent Publication No. 3(1991)-238441. The proposed radiation image recording and read-out apparatuses comprise: i) a circulation and conveyance means for conveying at least a single stimulable phosphor sheet along a circulation path, ii) an image recording section, which is located in the circulation path and in which a radiation image of an object is stored on the stimulable phosphor sheet, iii) an image read-out section, which is located in the circulation path and in which the radiation image having been stored on the stimulable phosphor sheet is read out from the stimulable phosphor sheet, and iv) an erasing section, which is located in the circulation path and in which energy remaining on the stimulable phosphor sheet is released after the radiation image has been read out therefrom.

Also, as disclosed in, for example, U.S. Pat. No. 4,855,598, techniques for carrying out energy subtraction processing on radiation images have heretofore been known.

When energy subtraction processing is to be carried out, a plurality of radiation images are recorded under different conditions of energy absorption characteristics with respect to radiation such as X-rays, $\alpha$-rays, $\beta$-rays, $\gamma$-rays, cathode rays or ultraviolet rays. The radiation images are then photoelectrically read out, and digital image signals which represent the radiation images are thereby obtained. The image signal components of the digital image signals, which represent corresponding picture elements in the radiation images, are then subtracted from each other, and a difference signal is thereby obtained which represents the image of a specific structure or part of the object represented by the radiation images, the specific structure having energy absorption characteristics different from those of the other structures of the object. With the energy subtraction processing method, a plurality of digital image signals are subtracted from each other, and a difference signal is thereby obtained. The radiation image of a specific structure of the object can then be reproduced from the difference signal.

Specifically, with the energy subtraction processing method, an object is exposed to several kinds of radiation having different energy distributions. Alternatively, the energy distribution of the radiation carrying image information of an object, is changed after it has been irradiated onto one of at least two radiation image recording media, after which the radiation impinges upon the second radiation image recording medium. In this manner, at least two radiation images, in which different images of a specific structure of the object are embedded, are obtained. Thereafter, the image signals representing at least two radiation images are weighted appropriately, when necessary, and subjected to a subtraction process, and the image of the specific structure of the object is thereby extracted.

In cases where energy subtraction processing is to be carried out by using stimulable phosphor sheets, radiation images may be stored on at least two stimulable phosphor sheets so that the parts of the radiation images corresponding to a specific structure of an object may be different in the at least two radiation images. Specifically, for example, a plate-shaped filter, which may be constituted of a metal, or the like, and which is capable of absorbing low energy components of radiation, may be located between two stimulable phosphor sheets, which are placed one upon the other. The two stimulable phosphor sheets, which are placed one upon the other with the filter intervening therebetween, may then be simultaneously exposed to radiation carrying image information of an object.

Techniques for carrying out superposition processing on radiation images have heretofore been disclosed in, for example, U.S. Pat. No. 4,356,398. In general, radiation images are used for diagnoses of illnesses and for other purposes. When a radiation image is used for such purposes, it is required that even small differences in the radiation energy absorption characteristics among structures of an object can be detected accurately in the radiation image. The extent, to which such differences in the radiation energy absorption characteristics can be detected in a radiation image, is referred to as the contrast detection performance or simply as the detection performance. A radiation image having better detection performance has better image quality and can serve as a more effective tool in, particularly, the efficient and accurate diagnosis of an illness.

Therefore, in order for the image quality to be improved, it is desirable that the detection performance of the radiation image may be enhanced. Practically, the detection performance is adversely affected by various noises.

Specifically, in radiation image recording systems using stimulable phosphor sheets, it has been found that the noises described below occur during the step for recording a radiation image on a stimulable phosphor sheet and reading out the radiation image therefrom.

(1) A quantum noise of radiation produced by a radiation source.

(2) A noise due to nonuniformity in how a stimulable phosphor coated on the stimulable phosphor sheet is distributed or how stimulable phosphor grains are distributed on the stimulable phosphor sheet.

(3) A noise of stimulating rays, which cause the stimulable phosphor sheet to emit light in proportion to the amount of energy stored thereon during its exposure to radiation.

(4) An electric noise in the means for detecting light, which is emitted by the stimulable phosphor sheet, and converting it into an electric signal.

(5) A noise of light emitted by the stimulable phosphor sheet.

Superposition processing is carried out in order to reduce the aforesaid noises markedly so that even small differences in the radiation energy absorption characteristics among structures of an object can be found accurately in a visible radiation image, which is reproduced finally, i.e. the detection performance of the radiation image can be improved markedly. Specifically, for example, two stimulable phosphor sheets, which are placed one upon the other, are simultaneously exposed to radiation, which has passed through an object. In this manner, two radiation images are stored on the stimulable phosphor sheets with the radiation having approximately identical energy distributions. Thereafter, the radiation images are photoelectrically read out from the stimulable phosphor sheets, and digital image signals representing the radiation images are thereby obtained. The digital image signals are weighted appropriately, and the image signal components of the weighted digital image signals, which represent corresponding picture elements in the radiation images, are then added to each other or averaged.

Specifically, in general, various noises described above exhibit different distributions for different radiation images stored on the stimulable phosphor sheets. When the image signals detected from the stimulable phosphor sheets are superposed one upon another, the noises can be averaged. Therefore, the noises become imperceptible in a superposition image, which is obtained from superposition processing. In this manner, the detection performance of the radiation image can be enhanced.

As described above, when radiation images for energy subtraction processing are to be obtained, a filter capable of absorbing low energy components of radiation should be located between two stimulable phosphor sheets, and the combination of the filter and the stimulable phosphor sheets should be set at the position for radiation image recording. Also, when radiation images for superposition processing are to be obtained, two stimulable phosphor sheets should be placed one upon the other, and the combination of the two stimulable phosphor sheets should be set at the position for radiation image recording. However, no apparatus for automatically carrying out such setting operations is available, and considerable time and labor are required to carry out the setting operations manually.

SUMMARY OF THE INVENTION

The primary object of the present invention is to provide a radiation image recording apparatus, with which radiation images to be subjected to energy subtraction processing and radiation images to be subjected to superposition processing can be obtained easily.

Another object of the present invention is to provide a radiation image recording and read-out apparatus, with which radiation images to be subjected to energy subtraction processing and radiation images to be subjected to superposition processing can be obtained easily.

The specific object of the present invention is to provide a cassette, with which radiation images to be subjected to energy subtraction processing and radiation images to be subjected to superposition processing can be obtained easily.

The present invention provides a first radiation image recording apparatus comprising a sheet housing section, which supports and houses at least a single stimulable phosphor sheet therein and which is exposed to radiation carrying image information of an object, a radiation image of the object being thereby stored on the stimulable phosphor sheet, which is housed in the sheet housing section, wherein the sheet housing section is divided into at least three sheet housing compartments by:
a) a radiation energy distribution separating filter, which has good absorption characteristics with respect to low energy components of radiation and which is located in a direction approximately normal to the direction of travel of the radiation carrying image information of the object, and
b) at least a single radiation transmitting member, which has good radiation transmitting characteristics and which is located parallel to the radiation energy distribution separating filter and at a position closer to the object than the radiation energy distribution separating filter is.

The present invention also provides a second radiation image recording apparatus, wherein the first radiation image recording apparatus in accordance with the present invention is modified such that each of the radiation energy distribution separating filter, the radiation transmitting member, and at least either one of a front side member, which constitutes an end face of the sheet housing section on the side close to the object, and a back side member, which constitutes an end face of the sheet housing section on the side remote from the object, is movable between an open position, which at least selectively opens each of the sheet housing compartments in order to allow the stimulable phosphor sheet to be fed into and out of each of the sheet housing compartments, and a closed position, which closes each of the sheet housing compartments in order for the radiation image to be stored on the stimulable phosphor sheet.

The present invention further provides a first radiation image recording and read-out apparatus comprising:
i) a circulation and conveyance means for conveying at least a single stimulable phosphor sheet, which is capable of storing a radiation image thereon, along a predetermined circulation path,
ii) an image recording section, which is located in the circulation path and provided with a sheet housing section for supporting and housing the stimulable phosphor sheet therein, and in which the stimulable phosphor sheet is exposed to radiation carrying image information of an object, a radiation image of the object being thereby stored on the stimulable phosphor sheet,
iii) an image read-out section, which is located in the circulation path and provided with:
a) a stimulating ray source for producing stimulating rays to be irradiated to the stimulable phosphor sheet, on which the radiation image was stored in the image recording section, the stimulating rays causing the stimulable phosphor sheet to emit light in proportion to the amount of energy stored thereon during its exposure to the radiation, and
b) a photoelectric read-out means for detecting the emitted light and obtaining an image signal representing the radiation image, and
iv) an erasing section, which is located in the circulation path and in which energy remaining on the stimulable phosphor sheet after the image signal has been obtained therefrom in the image read-out section is released before a next radiation image is stored on the stimulable phosphor sheet, wherein the sheet housing section is divided into at least three sheet housing compartments by:
a) a radiation energy distribution separating filter, which has good absorption characteristics with respect to low energy components of radiation and which is located in a direction approximately normal to the direction of travel of the radiation carrying image information of the object, and
b) at least a single radiation transmitting member, which has good radiation transmitting characteristics and which is located parallel to the radiation energy distribution separating filter and at a position closer to the object than the radiation energy distribution separating filter is, and
at least either one of the image recording section and the circulation and conveyance means is provided with a sheet distributing means, which selectively feeds the stimulable phosphor sheet into one of at least three sheet housing compartments.

The present invention still further provides a second radiation image recording and read-out apparatus, wherein the first radiation image recording and read-out apparatus in accordance with the present invention is modified such that the image recording section is provided with a feed-in opening, through which the stimulable phosphor sheet is fed into each of the sheet housing compartments, and a feed-out opening, through which the stimulable phosphor sheet is fed out from each of the sheet housing compartments, the feed-in opening and the feed-out opening being located adjacent to each other at one end of the image recording section, and each of the radiation energy distribution separating filter, the radiation transmitting member, and at least either one of a front side member, which constitutes an end face of the sheet housing section on the side close to the object, and a back side member, which constitutes an end face of the sheet housing section on the side remote from the object, is movable between an open position, which at least selectively opens each of the sheet housing compartments in order to allow the stimulable phosphor sheet to be fed into and out of each of the sheet housing compartments, and a closed position, which closes each of the sheet housing compartments in order for the radiation image to be stored on the stimulable phosphor sheet.

The present invention also provides a cassette for housing at least a single stimulable phosphor sheet therein and for use by being located at a position, which is exposed to radiation carrying image information of an object, the cassette comprising a box member provided with an opening, through which the stimulable phosphor sheet is to be fed into and out of the box member, and a cover member, which opens and closes the opening of the box member, wherein a region inside of the box member is divided into at least three sheet housing compartments by:
a) a radiation energy distribution separating filter, which has good absorption characteristics with respect to low energy components of radiation and which is located in a direction approximately normal to the direction of travel of the radiation carrying image information of the object, and b) at least a single radiation transmitting member, which has good radiation transmitting characteristics and which is located parallel to the radiation energy distribution separating filter and at a position closer to the object than the radiation energy distribution separating filter is.

Specifically, in the first and second radiation image recording apparatuses, the first and second radiation image recording and read-out apparatuses, and the cassette in accordance with the present invention, the sheet housing section for housing at least a single stimulable phosphor sheet therein is divided by at least two partitioning members into at least three sheet housing compartments. Of at least two partitioning members, the partitioning member, which is located on the side remotest from the object, is constituted of the radiation energy distribution separating filter, which has good absorption characteristics with respect to low energy components of radiation. At least a single other partitioning member is constituted of the radiation transmitting member, which has good radiation transmitting characteristics. To each of at least two sheet housing compartments, which are located closer to the object than the radiation energy distribution separating filter is, the radiation carrying image information of the object goes such that it may undergo little decay in energy. Therefore, at least two sheet housing compartments, which are located closer to the object than the radiation energy distribution separating filter is, are exposed to the radiation having approximately identical energy distributions. To the sheet housing compartment, which is exposed to the radiation having passed through the radiation energy distribution separating filter, the radiation having the energy distribution, in which the low energy components of the radiation have been reduced by the radiation energy distribution separating filter, goes.

In the second radiation image recording apparatus and the second radiation image recording and read-out apparatus in accordance with the present invention, each of the sheet housing compartments is opened when the stimulable phosphor sheet is to be fed into and out of each of the sheet housing compartments. Each of the sheet housing compartments is closed during an operation for recording a radiation image. In this manner, the stimulable phosphor sheet can be easily fed into and out of each of the sheet housing compartments. In the second radiation image recording and read-out apparatus in accordance with the present invention, the feed-in opening and the feed-out opening of the image recording section are located adjacent to each other. Therefore, the second radiation image recording and read-out apparatus in accordance with the present invention can be kept compact.

The term "radiation energy distribution separating filter" as used herein means a member provided with a material, which is capable of absorbing low energy components of radiation, such as Cu, Fe, Cr, Ni, Zn, Mo, Sn, or Bi. The radiation energy distribution separating filter may be constituted of the material, which is capable of absorbing low energy components of radiation, alone. Alternatively, the radiation energy distribution separating filter may comprise a substrate, which is constituted of one of other materials, and the material, which is capable of absorbing low energy components of radiation and which is dispersed in the substrate.

The term "radiation transmitting member" as used herein means a member constituted of a material, which has a high radiation transmittance, such as C, or Al.

By way of example, the sheet housing section or the region inside of the cassette may be divided by the radiation energy distribution separating filter and the radiation transmitting member into three sheet housing compartments. In such cases, the sheet housing compartment, which is located on the side remotest from the object and downstream from the radiation energy distribution separating filter, is herein referred to as a first sheet housing compartment. The sheet housing compartment, which is located adjacent to the first sheet housing compartment with the radiation energy distribution separating filter intervening therebetween, is referred to as a second sheet housing compartment. Also, the sheet housing compartment, which is located adjacent to the second sheet housing compartment with the radiation transmitting member intervening therebetween, is referred to as a third sheet housing compartment.

When the radiation carrying image information of the object is irradiated to the sheet housing section or the cassette, the radiation goes to the third sheet housing compartment and the second sheet housing compartment without energy of the radiation decaying. The radiation, the low energy components of which have been absorbed by the radiation energy distribution separating filter, i.e. in which the high energy components have been emphasized, goes to the first sheet housing compartment.

Specifically, radiation images of the object are recorded with the two kinds of radiation having approximately identical energy distributions on the two stimulable phosphor sheets, which are respectively housed in the third sheet housing compartment and the second sheet housing compartment. Therefore, the radiation images stored on these two stimulable phosphor sheets can be used for superposition processing.

Also, radiation images of the object are recorded with the two kinds of radiation having different energy distributions on the two stimulable phosphor sheets, which are respectively housed in the third or second sheet housing compartment and the first sheet housing compartment. Therefore, the radiation images stored on these two stimulable phosphor sheets can be used for energy subtraction processing.

The sheet housing section or the cassette may be provided with two, three, or more radiation transmitting members, and a fourth sheet housing compartment, a fifth sheet housing compartment, ... may thereby be formed. Stimulable phosphor sheets may then be housed in the three or more sheet housing compartments other than the first sheet housing compartment and exposed to the radiation. In this manner, radiation images of the object can be recorded with the three or more kinds of radiation having approximately identical energy distributions on the stimulable phosphor sheets, which are respectively housed in the three or more sheet housing compartments other than the first sheet housing compartment. Therefore, the radiation images for multiple superposition processing can be obtained.

Further, a plain or ordinary radiation image can be stored on a stimulable phosphor sheet, which is housed in one of the sheet housing compartments.

As described above, with the radiation image recording apparatuses, the radiation image recording and read-out apparatuses, and the cassette in accordance with the present invention, a plain or ordinary radiation image, radiation images for superposition processing, and radiation images for energy subtraction processing can be recorded easily and selectively.

BRIEF DESCRIPTION OF THE DRAWINGS

FIG. 1 is a schematic view showing an embodiment of the radiation image recording apparatus in accordance with the present invention, FIGS. 2A, 2B, and 2C are explanatory views showing the effects of the embodiment of the radiation image recording apparatus shown in FIG. 1, FIGS. 3A and 3B are schematic views showing a different embodiment of the radiation image recording apparatus in accordance with the present invention, FIG. 4 is an explanatory view showing how a sheet distributing means of the embodiment of the radiation image recording apparatus shown in FIGS. 3A and 3B operates, FIG. 12 is a schematic view showing an example of a radiation image recording apparatus, in which the embodiment of the cassette shown in FIG. 10 is exposed to radiation.

DESCRIPTION OF THE PREFERRED EMBODIMENTS

Figure 5:
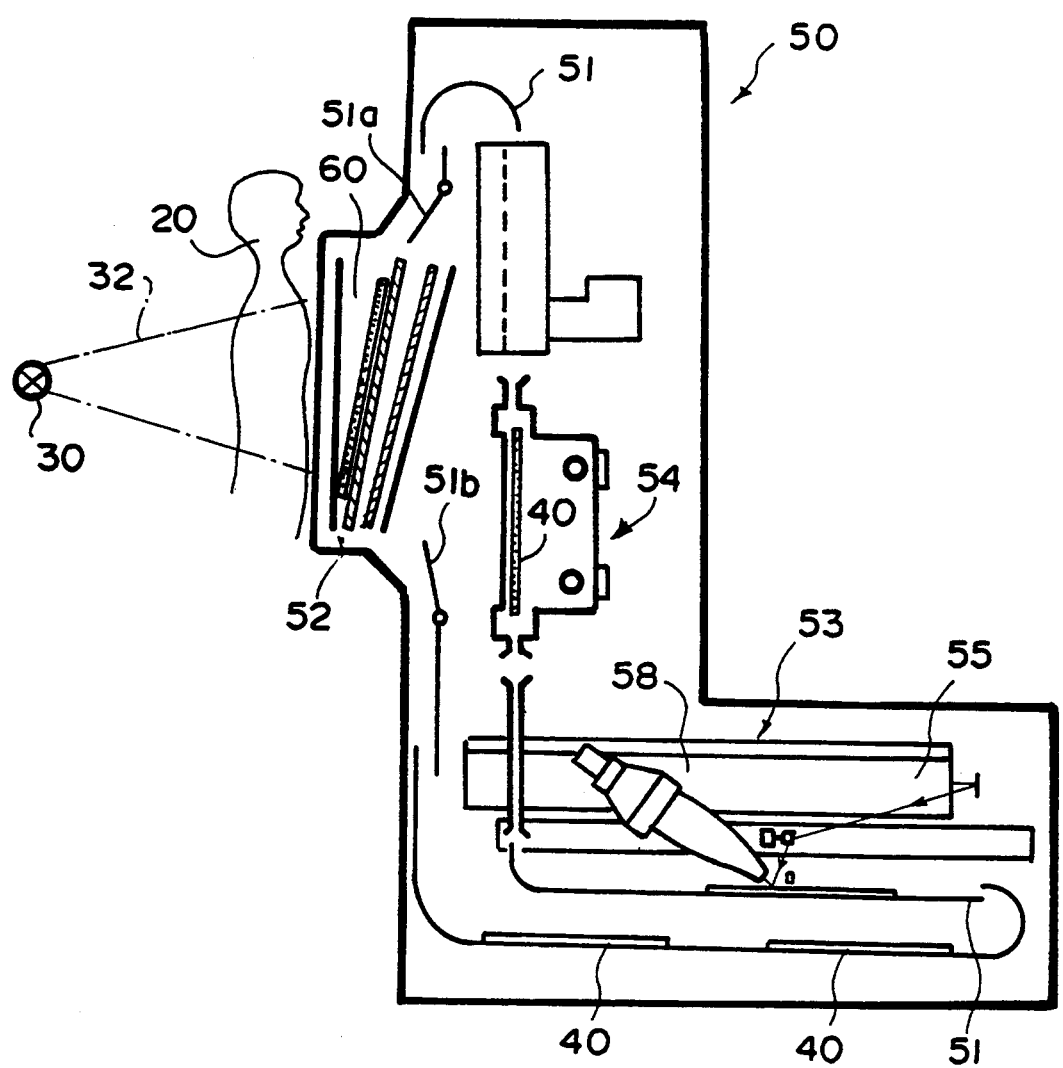
FIG. 5 is a schematic view showing an embodiment of the radiation image recording and read-out apparatus in accordance with the present invention.

The present invention will hereinbelow be described in further detail with reference to the accompanying drawings.

FIG. 1 is a schematic view showing an embodiment of the radiation image recording apparatus in accordance with the present invention. With reference to FIG. 1, a radiation image recording apparatus 10 comprises an object support base 12, which supports an object 20 thereon, and a sheet housing section 11, which houses a stimulable phosphor sheet 40 therein and which is exposed to radiation 30 having passed through the object 20. The sheet housing section 11 is provided with a radiation transmitting member 16, which is located on the side close to the object 20, and a radiation energy distribution separating filter 17, which is located on the side remote from the object 20. The sheet housing section 11 is divided by the radiation transmitting member 16 and the radiation energy distribution separating filter 17 into a first sheet housing compartment 13, which is located on the side remotest from the object 20, a second sheet housing compartment 14, which is adjacent to the first sheet housing compartment 13, and a third sheet housing compartment 15, which is located adjacent to the second sheet housing compartment 14 and on the side closest to the object 20.

How this embodiment of the radiation image recording apparatus operates will be described hereinbelow.

FIGS. 2A, 2B, and 2C are explanatory views showing the effects of the embodiment of the radiation image recording apparatus shown in FIG. 1. As illustrated in FIG. 2A, stimulable phosphor sheets 40, 40 are respectively inserted through an sheet feed-in opening (not shown) into the second sheet housing compartment 14 and the third sheet housing compartment 15. Thereafter, the radiation 32 is produced by a radiation source 30. The radiation 32 is irradiated to the object 20 lying on the object support base 12. The radiation 32, which has been irradiated to the object 20, passes through the object 20 and is then irradiated to the stimulable phosphor sheet 40, which is housed in the third sheet housing compartment 15. In this manner, a first radiation image K1 of the object 20 is stored on the stimulable phosphor sheet 40, which is housed in the third sheet housing compartment 15. Thereafter, the radiation 32 passes through the stimulable phosphor sheet 40, which is housed in the third sheet housing compartment 15, and the radiation transmitting member 16 such that energy of the radiation 32 may not decay. The radiation 32 is thus irradiated to the stimulable phosphor sheet 40, which is housed in the second sheet housing compartment 14. In this manner, a second radiation image K2 of the object is stored on the stimulable phosphor sheet 40, which is housed in the second sheet housing compartment 14.

In the manner described above, the first radiation image K1 and the second radiation image K2 are obtained with the radiation 32 having approximately identical energy distributions. Therefore, the two radiation images K1 and K2 can be used for superposition processing.

In the example shown in FIG. 2B, stimulable phosphor sheets 40, 40 are set respectively in the first sheet housing compartment 13 and the second sheet housing compartment 14. The radiation 32 is irradiated in the same manner as that shown in FIG. 2A, and a first radiation image M1 of the object 20 is stored on the stimulable phosphor sheet 40, which is housed in the second sheet housing compartment 14. Thereafter, low energy components of the radiation 32, which has passed through the stimulable phosphor sheet 40 housed in the second sheet housing compartment 14, are absorbed by the radiation energy distribution separating filter 17. The radiation 32, in which the low energy components have been reduced by the radiation energy distribution separating filter 17, is irradiated to the stimulable phosphor sheet 40, which is housed in the first sheet housing compartment 13. In this manner, a second radiation image M2 of the object 20 is stored on the stimulable phosphor sheet 40, which is housed in the first sheet housing compartment 13. Specifically, the second radiation image M2 is recorded with the radiation 32 having an energy distribution, in which the high energy components have been emphasized as compared with the energy distribution of the radiation 32 with which the first radiation image M1 was recorded.

Therefore, the two radiation images M1 and M2, which have been obtained in the manner described above, can be used for energy subtraction processing. As illustrated in FIG. 2C, such radiation images M1 and M2 capable of being used for energy subtraction processing can also be obtained by housing stimulable phosphor sheets 40, 40, respectively, in the first sheet housing compartment 13 and the third sheet housing compartment 15.

Also, a plane or ordinary radiation image is stored on the stimulable phosphor sheet 40, which is housed in either one of the second sheet housing compartment 14 and the third sheet housing compartment 15.

As described above, with the radiation image recording apparatus 10 in accordance with the present invention, the plain or ordinary radiation image, the radiation images for superposition processing, and the radiation images for energy subtraction processing can be obtained selectively.

FIGS. 3A and 3B are schematic views showing a different embodiment of the radiation image recording apparatus in accordance with the present invention. FIG. 4 is an explanatory view showing how a sheet distributing means of the embodiment of the radiation image recording apparatus shown in FIGS. 3A and 3B operates. With reference to FIGS. 3A, 3B, and FIG. 4, a radiation image recording apparatus 110 comprises a case housing 111 provided with a sheet feed-in opening 111a, through which a stimulable phosphor sheet 40 is fed into the case housing 111, and a sheet feed-out opening 111b, through which the stimulable phosphor sheet 40 is fed out of the case housing 111. The radiation image recording apparatus 110 also comprises a sheet housing section 112, which is located in the region inside of the case housing 111 and which is provided with a front plate 112a, a radiation transmitting member 116, a radiation energy distribution separating filter 117, and a back push plate 112b. The radiation image recording apparatus 110 further comprises a sheet distributing mechanism 120, which inclines the sheet housing section 112 from a position for image recording and moves the sheet housing section 112 to a position, at which the stimulable phosphor sheet 40 is selectively fed into each of sheet housing compartments as will be described later, and a position, at which the stimulable phosphor sheet 40 is fed out from each of the sheet housing compartments. The radiation image recording apparatus 110 still further comprises a sheet feed-out means 130 for feeding the stimulable phosphor sheet 40 out from each of the sheet housing compartments. The sheet housing section 112 is divided into a third sheet housing compartment 115, a second sheet housing compartment 114, and a first sheet housing compartment 113, which are located in this order from the upstream side of the radiation 32 coming from a radiation source (not shown). The third sheet housing compartment 115 is partitioned by the front plate 112a and the radiation transmitting member 116. The second sheet housing compartment 114 is partitioned by the radiation transmitting member 116 and the radiation energy distribution separating filter 117. The first sheet housing compartment 113 is partitioned by the radiation energy distribution separating filter 117 and the back push plate 112b. The sheet housing section 112 is located at the position for image recording, which is approximately normal to the direction, along which the radiation 32 travels from the left side in FIG. 3A. As illustrated in FIG. 4, the sheet distributing mechanism 120 comprises a rack plate 122, which is secured to an inner surface of the case housing 111, and a rack 122a, which is located on an upper end surface of the rack plate 122. The sheet distributing mechanism 120 also comprises a pinion 121, which is secured to the sheet housing section 112 and engaged with the rack 122a, a pulse motor (not shown) for driving the pinion 121, and a position control means (not shown) for the sheet housing section 112, which means generates an electric signal for driving the pulse motor.

How the embodiment of the radiation image recording apparatus shown in FIGS. 3A and 3B operates will be described hereinbelow.

As illustrated in FIG. 3A, the sheet housing section 112 is inclined by the sheet distributing mechanism 120 around a certain point below the sheet housing section 112 and in the direction indicated by the arrow E to the position, which is exactly below the sheet feed-in opening 111a, such that a desired sheet housing compartment, into which the stimulable phosphor sheet 40 is to be fed, may be brought to the position exactly below the sheet feed-in opening 111a. Specifically, as illustrated in detail in FIG. 4, the rack 122a, which is located on the upper end surface of the rack plate 122 secured to the inner surface of the case housing 111, engages with the pinion 121, which is secured to the sheet housing section 112 and is rotated by the pulse motor (not shown). The pulse motor is driven by the electric signal, which is received from the position control means (not shown) for the sheet housing section 112. The pinion 121, which is engaged with the rack 122a of the rack plate 122, is rotated by the pulse motor and is thereby moved along the upper end surface of the rack plate 122. At this time, because the pinion 121 is secured to the sheet housing section 112, the entire sheet housing section 112 is inclined to the position for sheet feed-in, which is shown in FIG. 3A.

While the sheet housing section 112 is being inclined from the position for image recording to the position for sheet feed-in, each of the sheet housing compartments is widened by a spring 123 so as to have a space capable of being inserted with the stimulable phosphor sheet 40. The stimulable phosphor sheet 40 is then inserted into the sheet housing compartment having been widened to the space capable of being inserted with the stimulable phosphor sheet 40. For example, in cases where radiation images for energy subtraction processing are to be obtained, this operation is repeated for the first sheet housing compartment 113 and the second sheet housing compartment 114. In cases where radiation images for superposition processing are to be obtained, this operation is repeated for the second sheet housing compartment 114 and the third sheet housing compartment 115. In cases where a single radiation image alone is to be obtained which need not be subjected to energy subtraction processing or superposition processing, the stimulable phosphor sheet 40 is inserted into only one of the three sheet housing compartments. In the same manner as that for the movement of the sheet housing section 112, the operation for moving each of the sheet housing compartments to the position exactly below the sheet feed-in opening 111a is carried out by driving the pulse motor with the electric signal generated by the position control means for the sheet housing section 112.

In the manner described above, the stimulable phosphor sheets 40, 40 are respectively housed in two of the three sheet housing compartments of the sheet housing section 112. Thereafter, the sheet housing section 112 is returned to the original position for image recording by operations reverse to the aforesaid operations. Specifically, the pulse motor is driven by the electric signal generated by the position control means for the sheet housing section 112, and the sheet housing section 112 is thereby moved reversely to the direction indicated by the arrow E and returned to the original position for image recording. Also, immediately before the sheet housing section 112 arrives at the position for image recording, the spring 123 is contracted, and the space between adjacent partition plates is narrowed. In this manner, the stimulable phosphor sheets 40, 40, which are respectively housed in the two sheet housing compartments, are sandwiched by the partition plates.

Thereafter, the radiation 32 is irradiated from the left side in FIG. 3A to the sheet housing section 112, which has been returned to the position for image recording. Radiation images are stored on the stimulable phosphor sheets 40, 40 in the same manner as that in the embodiment of FIG. 1. Specifically, radiation images for energy subtraction processing are stored on the stimulable phosphor sheets 40, 40, which are housed in the first sheet housing compartment 113 and the second sheet housing compartment 114. Also, radiation images for superposition processing are stored on the stimulable phosphor sheets 40, 40, which are housed in the second sheet housing compartment 114 and the third sheet housing compartment 115.

Thereafter, as illustrated in FIG. 3B, the sheet housing section 112, which houses the stimulable phosphor sheets 40, 40 having the radiation images stored thereon in the manner described above, is inclined by the sheet distributing mechanism 120 in the direction indicated by the arrow E to the position corresponding to the sheet feed-out opening 111b such that the sheet housing compartment, which houses the stimulable phosphor sheet 40 to be fed out, may be brought to the position exactly below the sheet feed-out opening 111b. This operation is carried out in the same manner as that of the operation for housing the stimulable phosphor sheet 40 in the sheet housing section 112.

Thereafter, the stimulable phosphor sheet 40 housed in the sheet housing compartment, which has been widened by the spring 123, is fed out through the sheet feed-out opening 111b by the sheet feed-out operation of the sheet feed-out means 130. Specifically, as illustrated in FIG. 4, a bearing 131 is rotated in the direction indicated by the arrow G, and a link 132 is thereby rotated in the direction indicated by the arrow F. A sheet push-up member 133, which is secured to an end of the link 132, pushes the lower end face of the stimulable phosphor sheet 40 housed in the sheet housing compartment. In this manner, the stimulable phosphor sheet 40 is fed out through the sheet feed-out opening 111b.

As described above, with the radiation image recording apparatus 110 in accordance with the present invention, the plain or ordinary radiation image, the radiation images for superposition processing, and the radiation images for energy subtraction processing can be obtained easily.

FIG. 5 is a schematic view showing an embodiment of the radiation image recording and read-out apparatus in accordance with the present invention. With reference to FIG. 5, a radiation image recording and read-out apparatus 50 comprises a circulation and conveyance means 51 for conveying at least a single stimulable phosphor sheet 40, which is capable of storing a radiation image thereon, along a predetermined circulation path. The radiation image recording and read-out apparatus 50 also comprises an image recording section 52, which is located in the circulation path and provided with a sheet housing section 60 for housing the stimulable phosphor sheet 40 therein. In the image recording section 52, the stimulable phosphor sheet 40 is exposed to radiation 32, which has been produced by a radiation source 30 and which has then passed through an object 20, and a radiation image of the object 20 is thereby stored on the stimulable phosphor sheet 40. The radiation image recording and read-out apparatus 50 further comprises an image read-out section 53, which is located in the circulation path. The image read-out section 53 is provided with a stimulating ray source 55 for producing stimulating rays to be irradiated to the stimulable phosphor sheet 40, on which the radiation image was stored in the image recording section 52, the stimulating rays causing the stimulable phosphor sheet 40 to emit light in proportion to the amount of energy stored thereon during its exposure to the radiation. The image read-out section 53 is also provided with a photoelectric read-out means 58 for detecting the emitted light and obtaining an image signal representing the radiation image. The radiation image recording and read-out apparatus 50 still further comprises an erasing section 54, which is located in the circulation path and in which energy remaining on the stimulable phosphor sheet 40 after the image signal has been obtained therefrom in the image read-out section 53 is released before a next radiation image is stored on the stimulable phosphor sheet 40.

Figure 6:
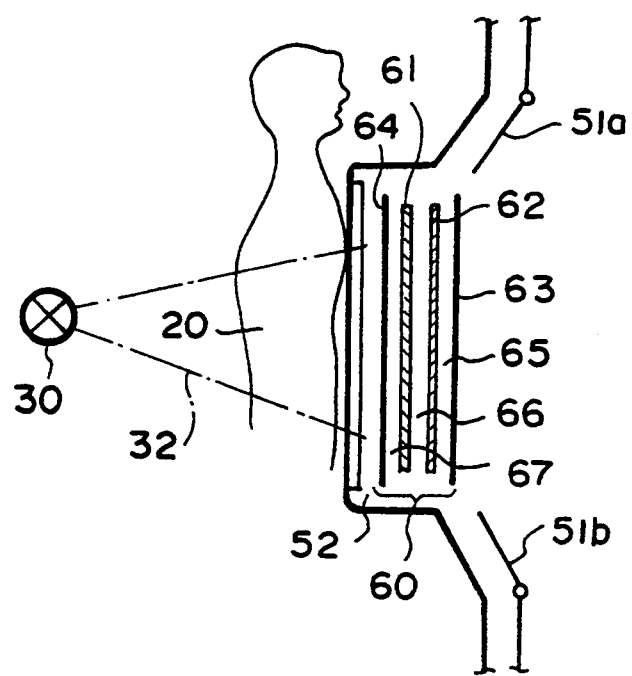
FIG. 6 is a detail view showing an image recording section in the embodiment of the radiation image recording and read-out apparatus shown in FIG. 5, FIGS. 7A, 7B, 7C, and 7D are explanatory views showing how stimulable phosphor sheets are fed into sheet housing compartments.

As illustrated in FIG. 6, the sheet housing section 60 of the image recording section 52 is provided with a radiation energy distribution separating filter 62, which has good absorption characteristics with respect to low energy components of the radiation 32 and which is located in a direction approximately normal to the direction of travel of the radiation 32 having passed through the object 20. The sheet housing section 60 is also provided with a radiation transmitting member 61, which has good radiation transmitting characteristics and which is located parallel to the radiation energy distribution separating filter 62 and at a position closer to the object 20 than the radiation energy distribution separating filter 62 is. The sheet housing section 60 is further provided with a sheet support member 63, which is located on the side rearward from the radiation energy distribution separating filter 62, and a sheet support member 64, which is located on the side forward from the radiation transmitting member 61. The sheet housing section 60 is thereby divided into a first sheet housing compartment 65, a second sheet housing compartment 66, and a third sheet housing compartment 67.

The circulation and conveyance means 51 is provided with a guide means 51a, which selectively feeds the stimulable phosphor sheet 40 into one of the three sheet housing compartments 65, 66, and 67, and a guide means 51b for guiding the stimulable phosphor sheet 40 when it is fed out of the sheet housing compartment. The guide means 51a and the guide means 51b constitute a sheet distributing means.

How this embodiment of the radiation image recording and read-out apparatus in accordance with the present invention operates will be described hereinbelow.

FIGS. 7A, 7B, 7C, and 7D are explanatory views showing how stimulable phosphor sheets are fed into sheet housing compartments. FIGS. 8A, 8B, 8C, and 8D are explanatory views showing how stimulable phosphor sheets are fed out of sheet housing compartments.

Figure 7:
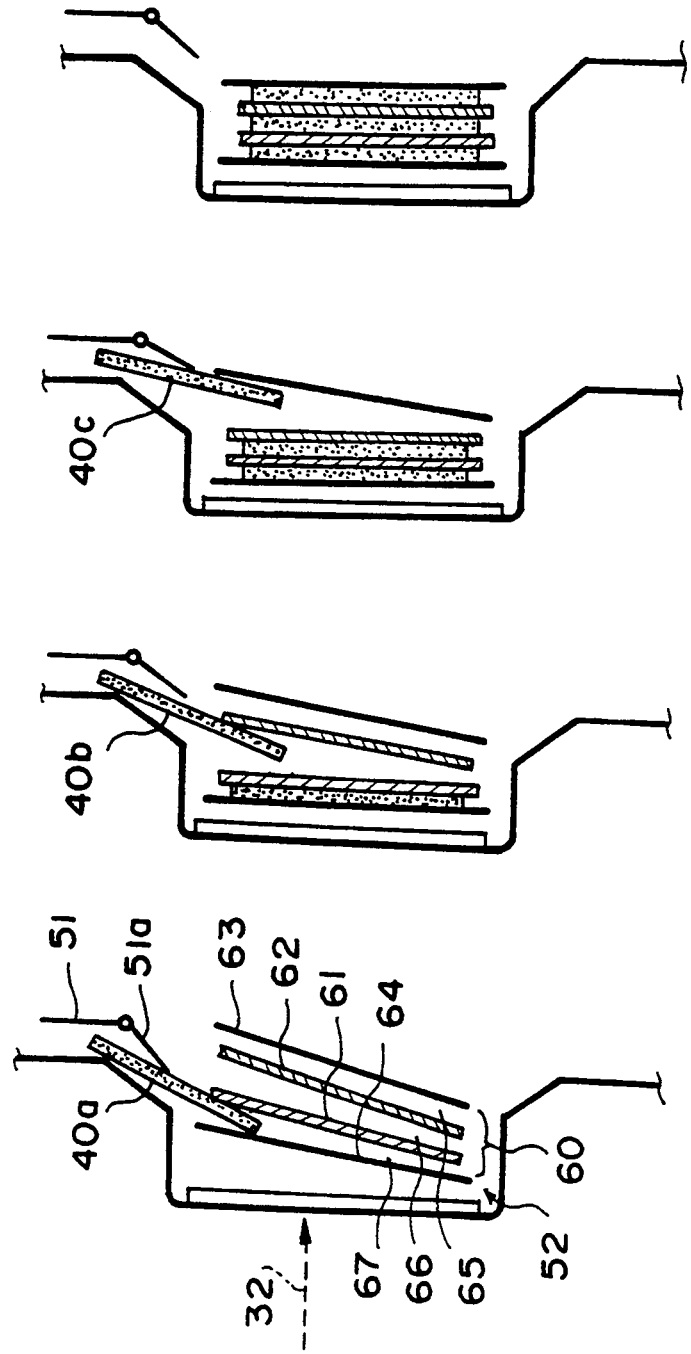

As illustrated in FIG. 7A, a first stimulable phosphor sheet 40a is conveyed by the circulation and conveyance means 51 along the predetermined circulation path into the image recording section 52. The first stimulable phosphor sheet 40a is then fed by the guide means 51a into the region (i.e. the third sheet housing compartment 67) between the sheet support member 64 and the radiation transmitting member 61, which region has been widened around its lower end. Thereafter, the sheet support member 64 and the radiation transmitting member 61 return to the positions, which are approximately normal to the direction of travel of the radiation 32, and the first stimulable phosphor sheet 40a is thereby held in the third sheet housing compartment 67. Thereafter, as illustrated in FIGS. 7B, 7C, and 7D, in the same manner as that described above, a second stimulable phosphor sheet 40b and a third stimulable phosphor sheet 40c, which are conveyed into the image recording section 52, are respectively fed into the second sheet housing compartment 66 and the first sheet housing compartment 65.

In the manner described above, the sheet feeding operation is carried out for all of the sheet housing compartments 65, 66, and 67 of the sheet housing section 60. Also, a stimulable phosphor sheet can be selectively fed by a selection means (not shown) into a desired sheet housing compartment.

As illustrated in FIG. 6, after stimulable phosphor sheets 40, 40, 40 have been fed into the image recording section 52 in the manner described above, the radiation 32 is irradiated via the object 20 to the image recording section 52. As in the radiation image recording apparatus 10 of FIG. 1, a single plain radiation image, two radiation images for superposition processing, and two radiation images for energy subtraction processing can be obtained on the stimulable phosphor sheets in accordance with the combination of the sheet housing compartments, in which the stimulable phosphor sheets are housed.

As illustrated in FIGS. 8A, 8B, 8C, and 8D, after the radiation images have been stored on the stimulable phosphor sheets, the stimulable phosphor sheets are sequentially fed out of the image recording section 52 and conveyed into the image read-out section 53.

Figure 8:
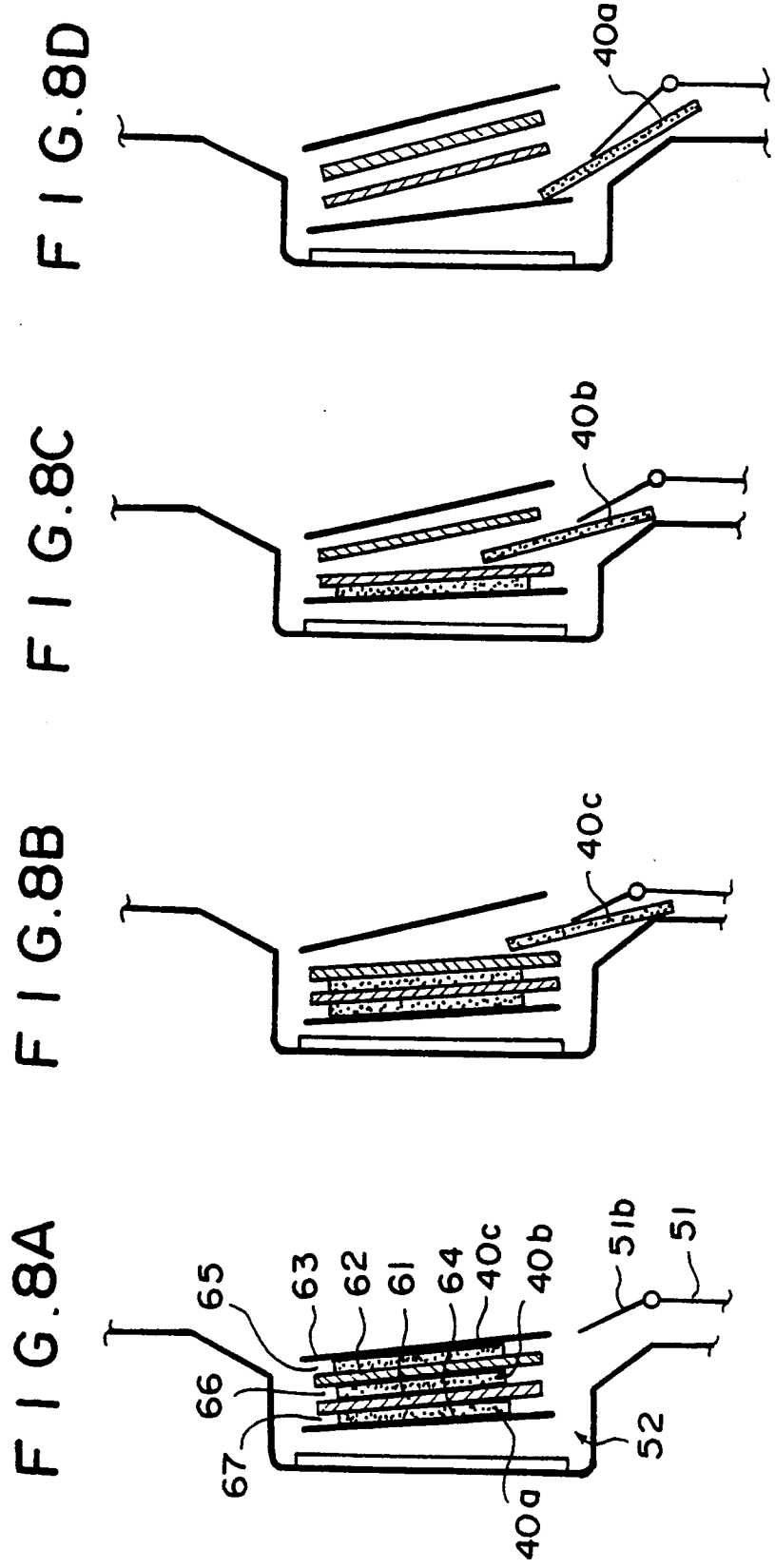
FIGS. 8A, 8B, 8C, and 8D are explanatory views showing how stimulable phosphor sheets are fed out of sheet housing compartments.

Specifically, as illustrated in FIG. 8A, the entire sheet housing section 60 is inclined around the upper ends of the sheet support means 63 and 64. Thereafter, as illustrated in FIG. 8B, the sheet support means 63 is inclined still further. The third stimulable phosphor sheet 40c is then guided by the guide means 51b and fed out of the image recording section 52. Thereafter, the radiation energy distribution separating filter 62 and the radiation transmitting member 61 are inclined one after the other, and the second stimulable phosphor sheet 40b and the first stimulable phosphor sheet 40a are fed out of the image recording section 52. The stimulable phosphor sheets 40c, 40b, and 40a are then conveyed by the circulation and conveyance means 51 into the image read-out section 53.

As described above, with the radiation image recording and read-out apparatus 50, the radiation images for superposition processing and the radiation images for energy subtraction processing can be obtained easily.

The radiation image recording and read-out apparatus in accordance with the present invention is not limited to the embodiment of FIG. 5. In particular, instead of being constituted of the guide means 51a and 51b, the sheet distributing means may be constituted of one of various other means, e.g. a mechanism which moves the sheet housing section 60 parallel to the direction of travel of the radiation 32 and selectively distributes the stimulable phosphor sheet 40 into a desired sheet housing compartment by adjusting the distance of movement of the sheet housing section 60.

Figure 9:
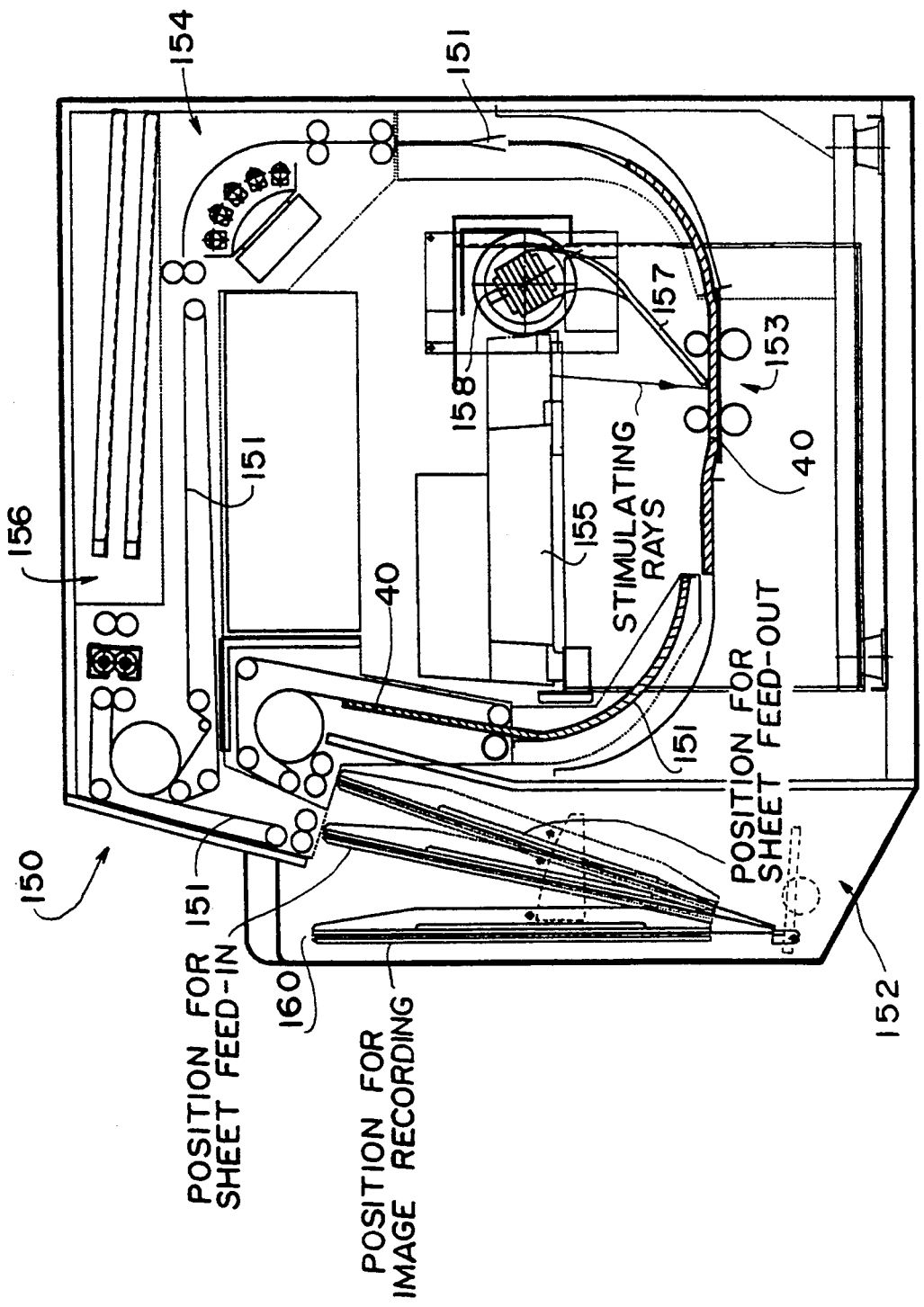
FIG. 9 is a schematic view showing a different embodiment of the radiation image recording and read-out apparatus in accordance with the present invention.

FIG. 9 is a schematic view showing a different embodiment of the radiation image recording and read-out apparatus in accordance with the present invention. With reference to FIG. 9, a radiation image recording and read-out apparatus 150 comprises a circulation and conveyance means 151 for conveying at least a single stimulable phosphor sheet 40, which is capable of storing a radiation image thereon, along a predetermined circulation path. The radiation image recording and read-out apparatus 150 also comprises an image recording section 152, which is located in the circulation path and provided with a sheet housing section 160 for housing the stimulable phosphor sheet 40 therein. In the image recording section 152, the stimulable phosphor sheet 40 is exposed to the radiation 32 (not shown in FIG. 9), and a radiation image is thereby stored on the stimulable phosphor sheet 40. The radiation image recording and read-out apparatus 150 further comprises an image read-out section 153, which is located in the circulation path. The image read-out section 153 is provided with a stimulating ray source 155 for producing stimulating rays to be irradiated to the stimulable phosphor sheet 40, on which the radiation image was stored in the image recording section 152, the stimulating rays causing the stimulable phosphor sheet 40 to emit light in proportion to the amount of energy stored thereon during its exposure to the radiation. The image read-out section 153 is also provided with a light guide member 157 and a photomultiplier 158 for detecting the emitted light and obtaining an image signal representing the radiation image. The radiation image recording and read-out apparatus 150 still further comprises an erasing section 154, which is located in the circulation path and in which energy remaining on the stimulable phosphor sheet 40 after the image signal has been obtained therefrom in the image read-out section 153 is released before a next radiation image is stored on the stimulable phosphor sheet 40. The radiation image recording and read-out apparatus 150 also comprises a stocker 156 for stocking the stimulable phosphor sheet 40, which has been caused to release remaining energy in the erasing section 154.

The image recording section 152 has the same structure as that of the radiation image recording apparatus 110 shown in FIGS. 3A, 3B and FIG. 4. Specifically, the image recording section 152 comprises a sheet housing section 160, which is provided with the front plate 112a, the radiation transmitting member 116, the radiation energy distribution separating filter 117, and the back push plate 112b. The image recording section 152 also comprises the sheet distributing mechanism 120, which moves the sheet housing section 160 from the position for image recording to the position for sheet feed-in and the position for sheet feed-out. The image recording section 152 further comprises the sheet feed-out means 130 for feeding the stimulable phosphor sheet 40 from each of the sheet housing compartments through a sheet feed-out opening (not shown) to the circulation path. The sheet housing section 160 is divided into the third sheet housing compartment 115, the second sheet housing compartment 114, and the first sheet housing compartment 113, which are located in this order from the upstream side of the radiation 32 coming from a radiation source (not shown). The third sheet housing compartment 115 is partitioned by the front plate 112a and the radiation transmitting member 116. The second sheet housing compartment 114 is partitioned by the radiation transmitting member 116 and the radiation energy distribution separating filter 117. The first sheet housing compartment 113 is partitioned by the radiation energy distribution separating filter 117 and the back push plate 112b. The sheet housing section 160 is located at the position for image recording, which is approximately normal to the direction, along which the radiation 32 travels from the left side in FIG. 9.

How the embodiment of the radiation image recording and read-out apparatus shown in FIG. 9 operates will be described hereinbelow.

Stimulable phosphor sheets 40, 40 are conveyed one after the other by the circulation and conveyance means 151 from the stocker 156 along the circulation path into the image recording section 152. In the same manner as that in the radiation image recording apparatus 110 shown in FIGS. 3A, 3B and FIG. 4, the stimulable phosphor sheets 40, 40 are distributed to and housed in the respective sheet housing compartments.

Thereafter, the radiation 32 is irradiated to the image recording section 152, in which the stimulable phosphor sheets 40, 40 are housed. As in the radiation image recording apparatus 110 shown in FIGS. 3A, 3B and FIG. 4, a single plain radiation image, two radiation images for superposition processing, and two radiation images for energy subtraction processing can be obtained on the stimulable phosphor sheets in accordance with the combination of the sheet housing compartments, in which the stimulable phosphor sheets are housed.

In the same manner as that in the radiation image recording apparatus 110 shown in FIGS. 3A, 3B and FIG. 4, the stimulable phosphor sheets 40, 40, on which the radiation images have been stored, are fed out one after the other through the sheet feed-out opening (not shown) of the image recording section 152 and conveyed by the circulation and conveyance means 151 along the predetermined circulation path into the image read-out section 153. Specifically, the first stimulable phosphor sheet 40 is conveyed into the image read-out section 153, and the second stimulable phosphor sheet 40 waits in the circulation path between the image recording section 152 and the image read-out section 153 until the first stimulable phosphor sheet 40 is conveyed out of the image read-out section 153.

The first stimulable phosphor sheet 40, which has been conveyed into the image read-out section 153, is exposed to the stimulating rays, which are produced by the stimulating ray source 155. Light, which is emitted by the first stimulable phosphor sheet 40 in proportion to the amount of energy stored thereon during its exposure to the radiation, is guided by the light guide member 157, which scans the first stimulable phosphor sheet 40. The guided light is converted by the photomultiplier 158 into an electric image signal. During the image read-out operation, the scanning of the first stimulable phosphor sheet 40 with the stimulating rays in the sub-scanning direction is effected by moving the first stimulable phosphor sheet 40 along the circulation path in the image read-out section 153 towards the erasing section 154.

At the time at which the image read-out operation is completed, the first stimulable phosphor sheet 40 is completely retracted from the image read-out section 153. The first stimulable phosphor sheet 40 is then conveyed along the predetermined circulation path into the erasing section 154. After the first stimulable phosphor sheet 40 has been completely retracted from the image read-out section 153, the second stimulable phosphor sheet 40, which waits in the circulation path, is conveyed into the image read-out section 153. The radiation image stored on the second stimulable phosphor sheet 40 is read out in the same manner as that described above.

The stimulable phosphor sheet 40, which has been conveyed into the erasing section 154, is exposed to visible light, and energy remaining thereon after the image signal has been detected therefrom is released. The stimulable phosphor sheet 40 is then conveyed along the predetermined circulation path into the stocker 156 and kept therein.

As described above, with the radiation image recording and read-out apparatus 150, the radiation images for superposition processing and the radiation images for energy subtraction processing can be obtained easily.

Also, the feed-in opening, through which the stimulable phosphor sheet 40 is fed into the image recording section 152, and the feed-out opening, through which the stimulable phosphor sheet 40 is fed out of the image recording section 152, are located adjacent to each other on the same side of the image recording section 152. Therefore, the radiation image recording and read-out apparatus can be kept compact.

In the radiation image recording and read-out apparatus 150, two stimulable phosphor sheets 40, 40 are circulated. However, the radiation image recording and read-out apparatus in accordance with the present invention is not limited to the processing of two stimulable phosphor sheets. For example, four stimulable phosphor sheets may be circulated in the radiation image recording and read-out apparatus. In such cases, the operation for recording radiation images on stimulable phosphor sheets can be carried out while the operation for reading out radiation images from the other stimulable phosphor sheets or the operation for erasing the other stimulable phosphor sheets are being carried out. Therefore, such a radiation image recording and read-out apparatus is advantageous for mass medical examinations wherein a large number of radiation images should be recorded quickly. Also, an ordinary plain radiation image can be obtained by circulating only a single stimulable phosphor sheet selectively.

Figure 10:
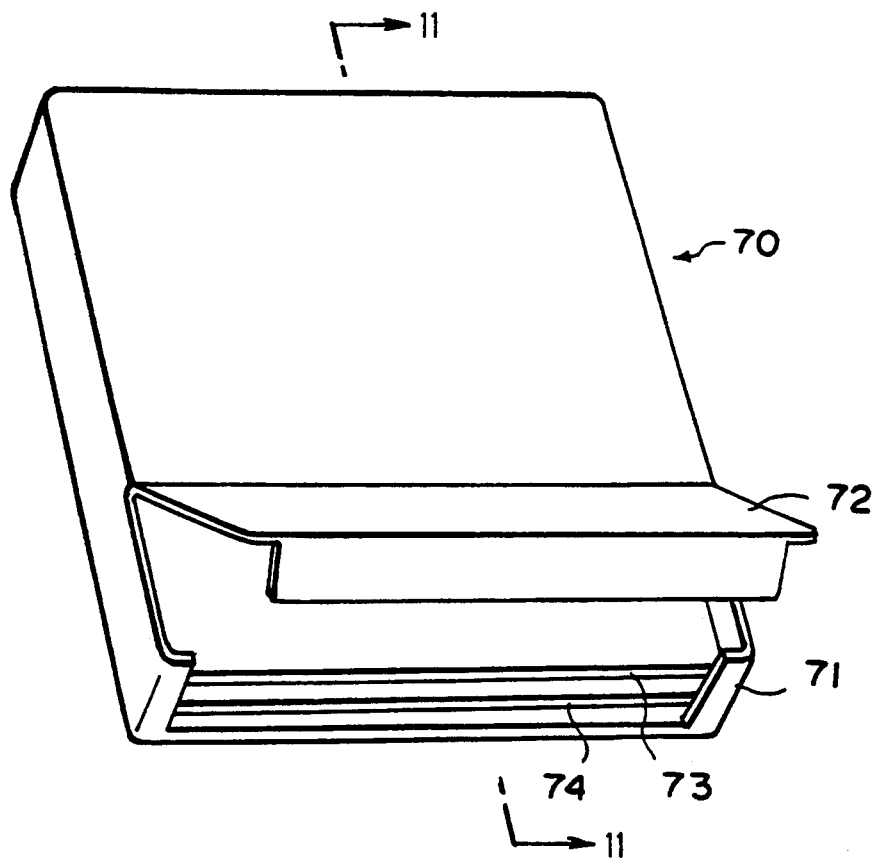
FIG. 10 is a schematic perspective view showing an embodiment of the cassette in accordance with the present invention.
Figure 11:
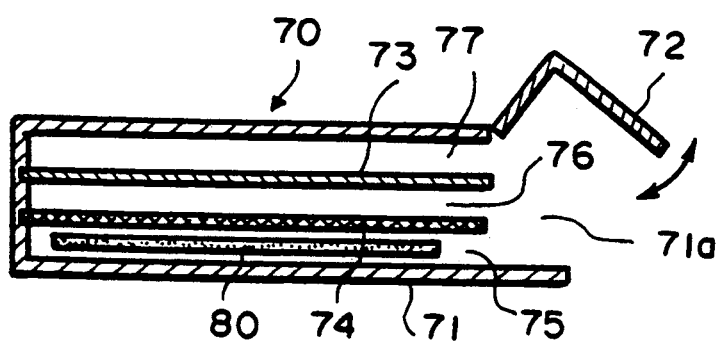
FIG. 11 is a sectional view taken along line 11–11 of FIG. 10.

FIG. 10 is a schematic perspective view showing an embodiment of the cassette in accordance with the present invention. FIG. 11 is a sectional view taken along line 11—11 of FIG. 10. With reference to FIGS. 10 and 11, a cassette 70 houses at least a single stimulable phosphor sheet 80 therein. The cassette 70 comprises a thin box member 71 provided with an opening 71a, through which the stimulable phosphor sheet 80 is to be fed into and out of the box member 71. The opening 71a is located on one end side of the box member 71. The cassette 70 also comprises a cover member 72, which opens and closes the opening 71a of the box member 71. As illustrated in FIG. 12, the cassette 70 is used by being housed in a cassette housing section 91 of a radiation image recording apparatus 90. The box member 71 and the cover member 72 may be constituted of, for example, a synthetic resin or FRP. A radiation transmitting member 73 and a radiation energy distribution separating filter 74 are located in the region inside of the cassette 70 such that they may approximately perpendicularly intersect with the direction of travel of the radiation 32, which has passed through the object 20 when the cassette 70 is housed in the cassette housing section 91 of the radiation image recording apparatus 90. The region (i.e. the sheet housing section) inside of cassette 70 is divided into three sheet housing compartments 75, 76, and 77 by the radiation transmitting member 73 and the radiation energy distribution separating filter 74.

As illustrated in FIG. 12, the cassette 70 is housed in the cassette housing section 91 of the radiation image recording apparatus 90 such that the radiation energy distribution separating filter 74 may be remoter from the object 20 than the radiation transmitting member 74 is. The radiation 32, which has passed through the object 20, is irradiated to the cassette 70. As a result, of the three sheet housing compartments 75, 76, and 77 divided in the region inside of the cassette 70, the third sheet housing compartment 77, which is closest to the object 20, and the second sheet housing compartment 76, which is adjacent to the third sheet housing compartment 77 with the radiation transmitting member 20 intervening therebetween, are exposed to the radiation having energy distributions, in which energy of the radiation 32 has not decayed.

The first sheet housing compartment 75, which is adjacent to the second sheet housing compartment 76 with the radiation energy distribution separating filter 74 intervening therebetween, is exposed to the radiation having an energy distribution, in which the low energy components of the radiation 32 have been absorbed by the radiation energy distribution separating filter 74.

Therefore, in cases where stimulable phosphor sheets 80, 80 are housed in the third sheet housing compartment 77 and the second sheet housing compartment 76 and exposed to the radiation 32 in the same manner as that described above, radiation images are stored with the radiation having approximately identical energy distributions on the stimulable phosphor sheet 80, which is housed in the third sheet housing compartment 77, and the stimulable phosphor sheet 80, which is housed in the second sheet housing compartment 76. These approximately identical radiation images can be used during superposition processing.

In cases where stimulable phosphor sheets 80, 80 are housed in the first sheet housing compartment 75 and the second sheet housing compartment 76 or the third sheet housing compartment 77 and exposed to the radiation 32 in the same manner as that described above, a radiation image is stored on the stimulable phosphor sheet 80, which is housed in the first sheet housing compartment 75, with the radiation having an energy distribution, in which the high energy components of the radiation 32 have been emphasized as compared with the radiation impinging upon the stimulable phosphor sheet 80 housed in the second sheet housing compartment 76 or the third sheet housing compartment 77. The radiation images obtained with the two kinds of radiation having different energy distributions can be used for energy subtraction processing.

As described above, with this embodiment of the cassette in accordance with the present invention, two of the three sheet housing compartments in the region inside of the cassette may be selected, and stimulable phosphor sheets may be housed in the two selected sheet housing compartments. The cassette may then be exposed to the radiation. In this manner, radiation images, which can be subjected to superposition processing, and radiation images, which can be subjected to energy subtraction processing, can be obtained easily and selectively. The radiation image recording operations for superposition processing and energy subtraction processing, which have heretofore required considerable time and labor, can be carried out easily.

The cassette in accordance with the present invention is not limited to the aforesaid embodiment wherein the opening is formed on one end side of the box member. The cassette in accordance with the present invention may have any structure, in which an opening for allowing a stimulable phosphor sheet to be fed into and out of the cassette is formed at a portion of the box member, and which has a cover member capable of being opened and closed and capable of closing the opening when it is closed. For example, the cassette may be constituted such that the entire area of the back surface of the box member may be open, and the cover member may cover the opening when it is closed.

What is claimed is:

1. A radiation image recording apparatus comprising a sheet housing section, which supports and houses at least a single stimulable phosphor sheet therein and which is exposed to radiation carrying image information of an object, a radiation image of the object being thereby stored on the stimulable phosphor sheet, which is housed in the sheet housing section,
   wherein the sheet housing section is divided into at least three sheet housing compartments by:
   a) a radiation energy distribution separating filter, which has good absorption characteristics with respect to low energy components of radiation and which is located in a direction approximately normal to the direction of travel of the radiation carrying image information of the object, and
   b) at least a single radiation transmitting member, which has good radiation transmitting characteristics and which is located parallel to said radiation energy distribution separating filter and at a position closer to the object than said radiation energy distribution separating filter is.

2. A radiation image recording apparatus as defined in claim 1 wherein each of said radiation energy distribution separating filter, said radiation transmitting member, and at least either one of a front side member, which constitutes an end face of the sheet housing section on the side close to the object, and a back side member, which constitutes an end face of the sheet housing section on the side remote from the object, is movable between an open position, which at least selectively opens each of said sheet housing compartments in order to allow the stimulable phosphor sheet to be fed into and out of each of said sheet housing compartments, and a closed position, which closes each of said sheet housing compartments in order for the radiation image to be stored on the stimulable phosphor sheet.

3. A radiation image recording and read-out apparatus comprising:
   i) a circulation and conveyance means for conveying at least a single stimulable phosphor sheet, which is capable of storing a radiation image thereon, along a predetermined circulation path,
   ii) an image recording section, which is located in the circulation path and provided with a sheet housing section for supporting and housing the stimulable phosphor sheet therein, and in which the stimulable phosphor sheet is exposed to radiation carrying image information of an object, a radiation image of the object being thereby stored on the stimulable phosphor sheet, iii) an image read-out section, which is located in the circulation path and provided with:
   a) a stimulating ray source for producing stimulating rays to be irradiated to the stimulable phosphor sheet, on which the radiation image was stored in the image recording section, the stimulating rays causing the stimulable phosphor sheet to emit light in proportion to the amount of energy stored thereon during its exposure to the radiation, and
   b) a photoelectric read-out means for detecting the emitted light and obtaining an image signal representing the radiation image, and iv) an erasing section, which is located in the circulation path and in which energy remaining on the stimulable phosphor sheet after the image signal has been obtained therefrom in the image read-out section is released before a next radiation image is stored on the stimulable phosphor sheet, wherein the sheet housing section is divided into at least three sheet housing compartments by:
   a) a radiation energy distribution separating filter, which has good absorption characteristics with respect to low energy components of radiation and which is located in a direction approximately normal to the direction of travel of the radiation carrying image information of the object, and
   b) at least a single radiation transmitting member, which has good radiation transmitting characteristics and which is located parallel to said radiation energy distribution separating filter and at a position closer to the object than said radiation energy distribution separating filter is, and at least either one of the image recording section and the circulation and conveyance means is provided with a sheet distributing means, which selectively feeds the stimulable phosphor sheet into one of at least three sheet housing compartments.

4. A radiation image recording and read-out apparatus as defined in claim 3 wherein the image recording section is provided with a feed-in opening, through which the stimulable phosphor sheet is fed into each of the sheet housing compartments, and a feed-out opening, through which the stimulable phosphor sheet is fed out from each of the sheet housing compartments, said feed-in opening and said feed-out opening being located adjacent to each other at one end of the image recording section, and each of said radiation energy distribution separating filter, said radiation transmitting member, and at least either one of a front side member, which constitutes an end face of the sheet housing section on the side close to the object, and a back side member, which constitutes an end face of the sheet housing section on the side remote from the object, is movable between an open position, which at least selectively opens each of said sheet housing compartments in order to allow the stimulable phosphor sheet to be fed into and out of each of said sheet housing compartments, and a closed position, which closes each of said sheet housing compartments in order for the radiation image to be stored on the stimulable phosphor sheet.

5. A cassette for housing at least a single stimulable phosphor sheet therein and for use by being located at a position, which is exposed to radiation carrying image information of an object, the cassette comprising a box member provided with an opening, through which the stimulable phosphor sheet is to be fed into and out of the box member, and a cover member, which opens and closes the opening of the box member, wherein a region inside of the box member is divided into at least three sheet housing compartments by:
   a) a radiation energy distribution separating filter, which has good absorption characteristics with respect to low energy components of radiation and which is located in a direction approximately normal to the direction of travel of the radiation carrying image information of the object, and
   b) at least a single radiation transmitting member, which has good radiation transmitting characteristics and which is located parallel to said radiation energy distribution separating filter and at a position closer to the object than said radiation energy distribution separating filter is.

* * * * *